United States Patent
Mishima et al.

(10) Patent No.: US 8,288,164 B2
(45) Date of Patent: Oct. 16, 2012

(54) REACTION CUVETTE FOR AUTOMATIC ANALYZER AND METHOD OF SURFACE TREATMENT FOR REACTION CUVETTE

(75) Inventors: Hiroyuki Mishima, Hitachinaka (JP); Hiroaki Ishizawa, Hitachinaka (JP); Masashi Endo, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 695 days.

(21) Appl. No.: 12/120,458

(22) Filed: May 14, 2008

(65) Prior Publication Data
US 2008/0311001 A1  Dec. 18, 2008

(30) Foreign Application Priority Data
May 15, 2007  (JP) ................................. 2007-129289

(51) Int. Cl.
*B01L 3/14* (2006.01)
(52) U.S. Cl. .............. 436/135; 422/186.07; 422/186.04; 422/547; 436/807; 204/176; 204/164
(58) Field of Classification Search .................. 422/102, 422/186.04–186.05, 186.07–186.09, 186.22, 422/547; 436/135, 807; 204/164, 176, 206, 204/224 R; 73/864.91
See application file for complete search history.

(56) References Cited

U.S. PATENT DOCUMENTS

| | | | |
|---|---|---|---|
| 5,229,163 A | | 7/1993 | Fox |
| 5,458,856 A | * | 10/1995 | Marie et al. .................... 422/186 |
| 5,587,131 A | * | 12/1996 | Malkin et al. ............ 422/186.11 |
| 2005/0047970 A1 | * | 3/2005 | Amo et al. .................... 422/102 |

FOREIGN PATENT DOCUMENTS

| | | |
|---|---|---|
| EP | 0 014 797 | 9/1980 |
| EP | 1 595 605 | 11/2005 |
| EP | 1 717 585 | 11/2006 |
| JP | 2005-077263 | 3/2005 |
| JP | 2006-125897 | 5/2006 |

* cited by examiner

*Primary Examiner* — Jill Warden
*Assistant Examiner* — Cedric Chan
(74) *Attorney, Agent, or Firm* — Mattingly & Malur, PC

(57) ABSTRACT

The present invention provides a highly reliable reaction cuvette in which air bubbles are adhered little and mutual contamination can be prevented among samples and reagents in adjoining reaction cuvettes, a method of surface treatment for a reaction cuvette, and an automatic analyzer with the reaction cuvette mounted therein. The reaction cuvette according to the present invention, in which a sample and a reagent are mixed with each other and its concentration is measured, has an area subjected to hydrophilic treatment by electric discharging on inner and outer surfaces of the reaction cuvette. Further the reaction cuvette has a container-like form with its upper portion opened to provide an opening and its lower portion closed to provide a bottom. The hydrophilic area is present from a bottom of the reaction cuvette up to a midway to the opening.

16 Claims, 9 Drawing Sheets

REACTION CUVETTE FOR AUTOMATIC ANALYZER AND METHOD OF SURFACE TREATMENT FOR REACTION CUVETTE

BACKGROUND OF THE INVENTION

1. Field of the Invention

The present invention relates to a reaction cuvette for an automatic analyzer for measuring a concentration of a test article in a sample, a method of surface treatment for a reaction cuvette for an automatic analyzer, and an automatic analyzer having the cuvette.

2. Description of the Related Art

One of the problems in the field of automatic analyzers is reduction of amounts of samples and regents used.

With the tendency for increase of analytical items, an amount of samples used for each discrete analytical item becomes smaller and analysis of a minute amount of samples is generally performed as a routine work.

Also reduction of amounts of samples and regents used is required in terms of reagent cost and their disposed amounts.

A new problem has occurred that has not been experienced to satisfy the need for such reduction.

Even in the conventional technology, there is the possibility that air bubbles generated by agitation or the like and adhered on an inner wall of a reaction cuvette interfere with an optical axis of a light beam passing through the reaction cuvette because of a downsized reaction cuvette.

Especially, the air bubbles adhered at four corners of a bottom portion of the reaction cuvette may not easily be removed because the air bubbles are supported by two wall surfaces and the bottom surface. When air bubbles are generated, an incoming light beam is scattered by the air bubbles adhered on the reaction cuvette and the degree of scattering cannot be ignored.

Furthermore, there is another necessity of reducing an amount of water used for cleaning the reaction cuvette and remaining still in the reaction cuvette even after cleaning in association with reduction of an amount of a reagent liquid used in testing.

There has been proposed a method of making inner wall of a reaction cuvette hydrophilic to overcome the problems described above. Effective methods for making resin surface hydrophilic include the oxygen plasma treatment, ozone treatment, ozone water treatment, and corona discharge treatment.

In relation to the technical tendency described above, there has been examined the possibility of making inner walls of a reaction cuvette hydrophilic with ozone water. As disclosed in JP-A-2005-77263, if ozone water which is a liquid is used, the entire surfaces of a reaction cuvette can be made hydrophilic, and thereby air bubbles are prevented from adhering to inner walls and a bottom portion of the reaction cuvette.

With the technique, however, a resin is oxidized excessively, and the translucency becomes disadvantageously low. In an automatic analyzer, when optical absorbance of a reaction cuvette itself increases, a period in which the reaction cuvette can be used becomes disadvantageously short.

Furthermore, it is difficult to maintain a concentration of ozone water at a constant level, and complicated processes such as cleaning and drying are required after completion of the treatment.

When the entire are of inner walls of a reaction cuvette is made hydrophilic, another problem may occur that a reagent inside a reaction cuvette moves over a surface of the reaction cuvette into an adjoining one to cause mutual contamination and provide abnormal analytical results.

An extremely difficult work is required to contact ozone water with only desired areas for hydrophilic treatment.

JP-A-2006-125897 discloses a method of partially improving wettability. Specifically, this document proposes treatment with ozone water requiring masking with a complicated form for improving wettability of only a surface used on optical measurement on inner walls of a reaction cuvette.

There has also been examined the possibility of making inner walls of a reaction cuvette by spraying a gas containing ozone thereto.

SUMMARY OF THE INVENTION

The conventional techniques for making inner walls of a reaction cuvette hydrophilic have problems as follows. When inner walls of a reaction cuvette are sufficiently hydrophilic with ozone water to prevent air bubbles from adhering to the inner walls, a resin is degraded. When masking is performed to localize the areas to be made hydrophilic, inner walls of the reaction cuvette are physically damaged. When a liquid is used for making inner walls of a reaction cuvette hydrophilic, it is difficult to control an area of surfaces to be made hydrophilic.

In the method of spraying a gas containing ozone, the entire area of inner walls of a reaction cuvette is made hydrophilic, and the meniscus phenomenon occurs in which a sample liquid to be analyzed or measured creeps up on inner walls of a reaction cuvette. In this case, the phenomenon develops even an opening of the reaction cuvette, and the sample liquid may extend even to outside of the reaction cuvette.

An object of the present invention is to improve hydrophilicity of only required portions inside a reaction cuvette, and with the present invention, it is possible to prevent air bubbles from easily adhering to inner walls of a reaction cuvette and also to reduce amounts of a sample liquid and a reagent liquid required for testing.

The present invention provides a reaction cuvette for an automatic analyzer in which a sample and a reagent are mixed with each other and its concentration is measured, wherein the reaction cuvette has, on an inner surface thereof, an area subjected to surface treatment which makes the area hydrophilic by electric discharging.

The present invention also provides a method of performing a surface treatment of a reaction cuvette for an automatic analyzer in which a sample and a reagent are mixed with each other and its concentration is measured, the method comprising the steps of: providing a first electrode, which is inserted inside the reaction cuvette; providing second electrodes outside the reaction cuvette in such a manner that the second electrodes face each other; and making at least an inner surface of the reaction cuvette hydrophilic by electric discharging based on discharge generated by voltages applied to the first and second electrodes.

The present invention is described in further details below.

To achieve the objectives described above, in the present invention, an area of a reaction cuvette to be made hydrophilic is placed between the first electrode and the second electrode to be subjected to surface treatment by electric discharging.

Because a reaction cuvette is generally made of a resin and has a container-like form, the reaction cuvette may be used as a dielectric body, and arcing does not occur even when the electrodes is not coated with any specific material, and therefore the inner walls can easily and efficiently be made hydrophilic.

When the first electrode is inserted into the reaction cuvette, a counter electrode is approached to inner walls of the reaction cuvette, and therefore electric discharge occurs between the first electrode and an inner wall of the reaction cuvette and also between an outer wall of the reaction cuvette and the second electrodes facing each other, so that the both walls are made hydrophilic.

Furthermore, when the opposed second electrodes are placed between adjoining reaction cuvettes or on a bottom surface of a reaction cuvette, an area around the reaction cuvette or the bottom surface of the reaction cuvette can be made hydrophilic.

Because the electric discharging is performed in an atmosphere containing oxygen such as air, ozone, which is one type of active oxygen species, is also generated simultaneously. A half-life of ozone is quite large, namely several hours, and therefore ozone molecules remain within a reaction cuvette during and even after the treatment and oxidize unspecified portions of inner walls of the reaction cuvette. Therefore areas other than those facing the electrodes is subjected to hydrophilic treatment.

In addition, because ozone generated during the treatment adsorbs electrons emitted from the portion to which a voltage is applied, duration of electric discharge is suppressed disadvantageously.

To overcome the problems, the present invention provides a method of treatment for discharging a gas containing ozone within a reaction cuvette through a first electrode having an opening (referred to as a hollow electrode hereinafter) to preserve an atmosphere around the electrode in the constant state.

When a time for treatment is very short and a concentration of ozone is low, it is possible to discharge ozone in the reaction cuvette by introducing air into the reaction cuvette after the treatment. In this process, decomposition of ozone is promoted by increasing temperature of the gas to be introduced into the reaction cuvette to efficiently remove ozone.

It is also possible to provide a reaction cuvette with the opening facing downward for naturally discharging ozone without forcibly discharging the ozone-containing gas by using the hollow electrode, because dusts or other foreign materials are prevented from dropping into the inside of the reaction cuvette and ozone generated in electric discharge is heavier than air.

Furthermore, the hollow electrode can be used not only for discharging ozone, but also for introducing a process gas, which makes it easier to control a state of a gas in the reaction cuvette. The process gas is any of air, nitrogen, oxygen, a rare gas such as Ar, vapor, or of a mixture gas thereof.

The first electrode for a gas to flow has only to have an opening, and it is not limited to a cylindrical one, and may be pillar-like or similar to a form of the reaction cuvette.

A conductive metal such as aluminum, stainless steel, iron, copper, and tungsten may be used as a material for the electrode.

To be made partially hydrophilic, there is the method of making the first electrode thicker only in an area to be made hydrophilic to shorten a range between the opposed electrodes.

In this method, the smaller a reaction cuvette, the smaller a rod electrode to be inserted into the reaction cuvette, and therefore the method is suitable for a reaction cuvette with the size smaller than a certain value.

When the reaction cuvette is further minimized, by placing the counter electrode only in an area to be made hydrophilic, it is possible to generate electric discharge locally. With this configuration, the processing for making a desired area locally hydrophilic can be performed regardless of a form of the first electrode.

When a voltage is applied to a hollow electrode, an electric field is generated between the hollow electrode and the opposed electrodes, and electric discharge occurs; however because there is no electric field inside the hollow electrode, electric discharge does not occurs there.

When the hollow electrode is not moved toward a bottom of a reaction cuvette, electric discharge little occurs in an area where an internal peripheral surface of the hollow electrode is close to the bottom of the reaction cuvette. As a result, the area is not made hydrophilic.

In addition, when a voltage is applied to a hollow electrode in the state where a gas is made to flow in an upper portion of the reaction cuvette, it is possible to introduce into a reaction cuvette a gas ionized by corona discharge. With this technique, nonuniform electrification inside the reaction cuvette can be prevented, and surface treatment can always be performed in the stable state.

With the present invention, it is possible to prevent air bubbles from adhering to inner wall surfaces of a reaction cuvette to thereby perform analytical photometry with a high degree of reliability.

Furthermore it is possible to prevent areas other than a desired one from being made hydrophilic, which would otherwise be produced by secondary oxidization caused by ozone generated with electric discharge.

In addition, it is possible to overcome the problem in the conventional technology that adhesion of air bubbles onto a bottom of a reaction cuvette cannot be prevented by local improvement of a photometric surface (for making the surface hydrophilic), which contributes to improvement of analytical precision.

BRIEF DESCRIPTION OF THE DRAWINGS

FIG. 6 is a block diagram illustrating a configuration in which a first electrode having a rectangular opening is used in a sixth example of the present invention, and FIG. 6A is a front view, while

FIG. 7 is a block diagram illustrating a configuration in which a portion without an electric field of a hollow electrode is approached to a surface of a reaction cuvette in a seventh example of the present invention, and FIG. 7A is a front view, while

FIG. 8A shows the case where a portion of a bottom portion of a reaction cuvette has been subjected to the processing for making hydrophilic, while FIG. 8B shows the case where the same portion has not been subjected to the processing.

DETAILED DESCRIPTION OF THE PREFERRED EMBODIMENTS

Examples of the present invention are described in detail below with reference to the related drawings.

It is to be noted that the present invention is not limited to the examples described below.

EXAMPLE 1

Figure 1:
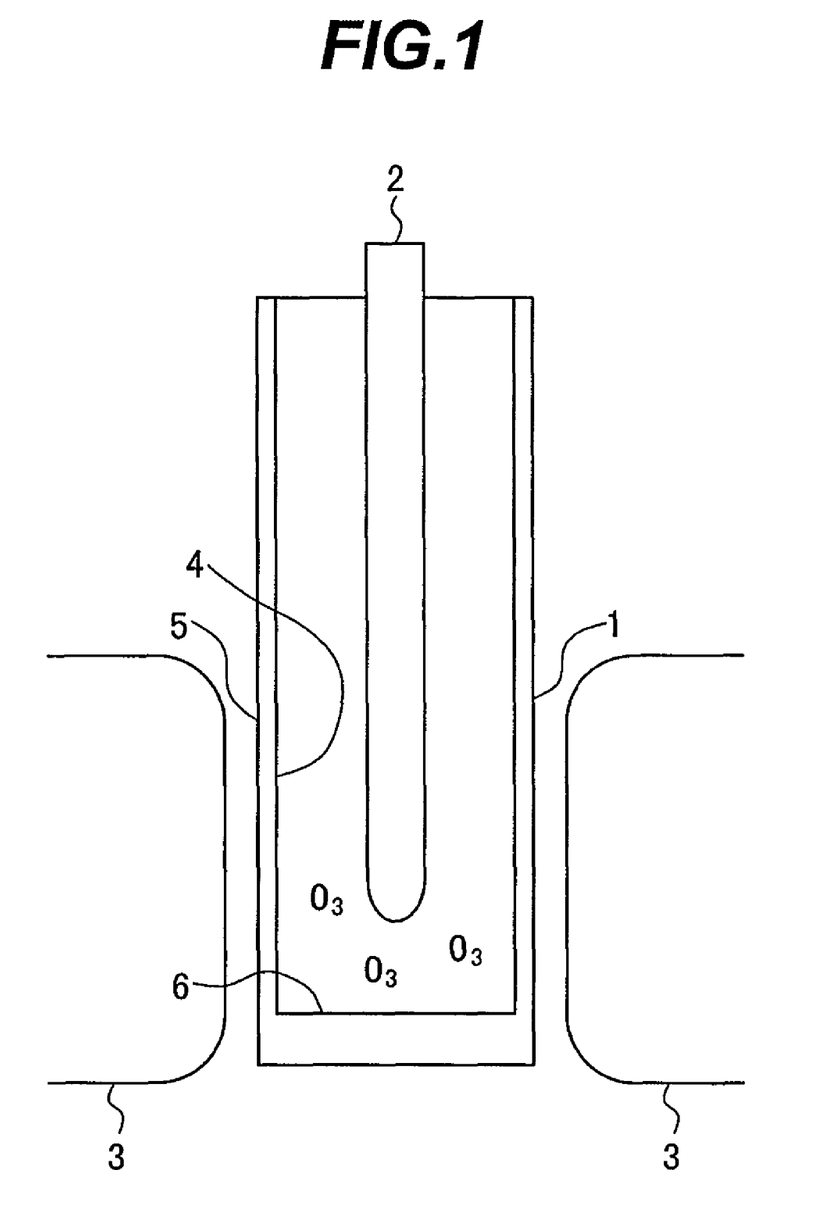
FIG. 1 is a view illustrating a positional relation between an electrode and a reaction cuvette in a first example of the present invention.

FIG. 1 is a view illustrating a basic layout of an electrode.

A first electrode 2 is inserted into a reaction cuvette 1, and second electrodes 3 facing each other are placed outside the reaction cuvette 1.

The first electrode is connected to a high voltage side of a high-voltage power supply, and the opposed second electrodes 3 are grounded.

A voltage is applied to a section between the first electrode 2 and the second electrode 3 to generate electric discharge between the electrodes.

An inner wall face 4 of the reaction cuvette, an outer wall face 5 of the reaction cuvette, and a bottom 6 of the reaction cuvette are made hydrophilic by making use of highly reactive radicals such as active oxygen species generated by electric discharge.

An amount of ozone, which is one type of active oxygen, increases in response to voltage application time. This ozone has a long life, stays in the reaction cuvette and oxidizes unspecified areas even after the completion of electric discharge.

As a result, portions other than an area between the first electrode 2 and the second electrode 2 are made hydrophilic, which leads to nonuniformity in product quality.

EXAMPLE 2

To solve the problem described above, an electrode 7 as shown in FIG. 2 is used instead of the electrode 2 shown in FIG. 1.

Figure 2:
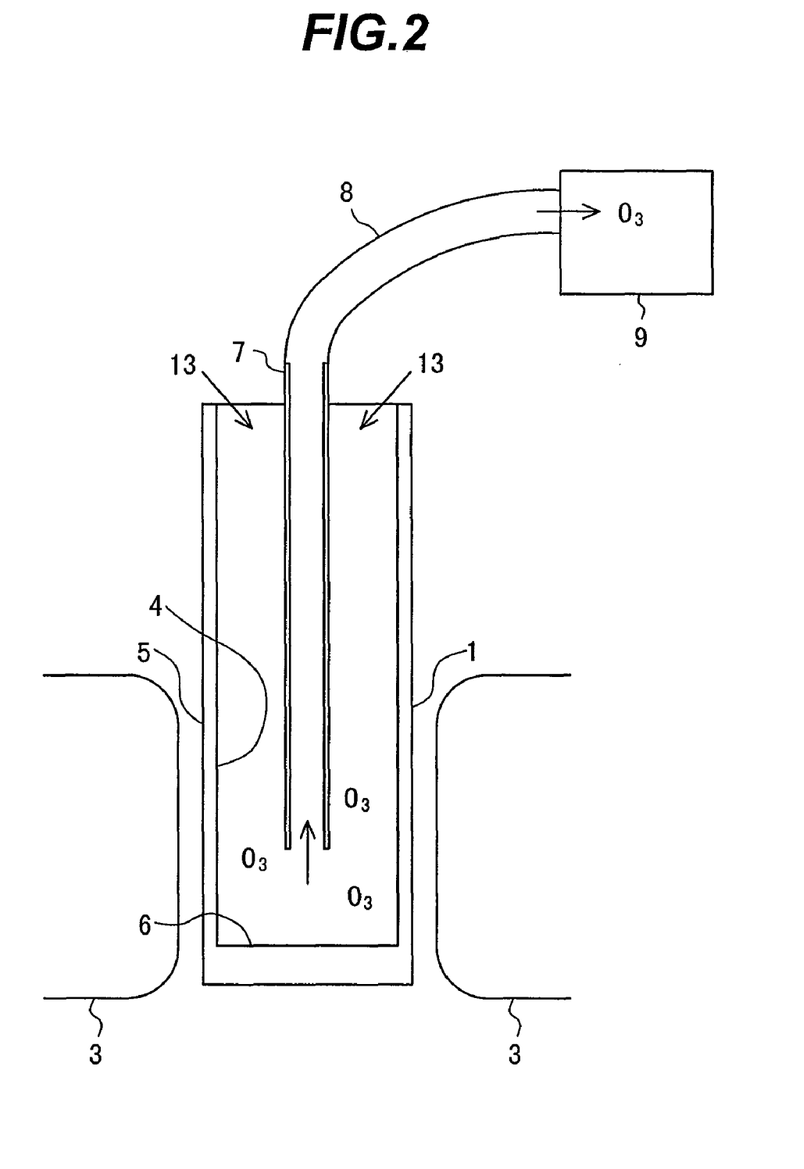
FIG. 2 is a block diagram illustrating a configuration in which ozone is discharged using a hollow electrode (a first embodiment) in a second example of the present invention.

Namely, ozone is discharged by the first electrode 7 which is hollow and has an opening at its lower end (Referred to as hollow electrode below). The hollow electrode 7 has a pipe-like form, and is inserted into the reaction cuvette 1.

A gas decomposer 9 is connected to the hollow electrode 7 with a piping 8. A high voltage is applied to a section between the 7 and the opposed second electrode 3 to generate electric discharge between the electrodes. During electric discharge, ozone 14 in the reaction cuvette 1 is sucked and discharged through the hollow electrode 7.

Thus, air not containing the ozone 14 always flows into the reaction cuvette 1, which prevents portions of the reaction cuvette 1 from being made unnecessarily hydrophilic.

A surface area subjected to the hydrophilic process has an advantage that air bubbles hardly adhere, but the meniscus phenomenon of a sample liquid may occur there, and the phenomenon may develop even to outside of the reaction cuvette. Therefore, it is preferable to replace, in places not to be subjected to the hydrophilic process, the air 13 containing ozone 14 with the air 13 not containing the ozone 14 so that the ozone 14 will not contact the places.

EXAMPLE 3

Figure 3:
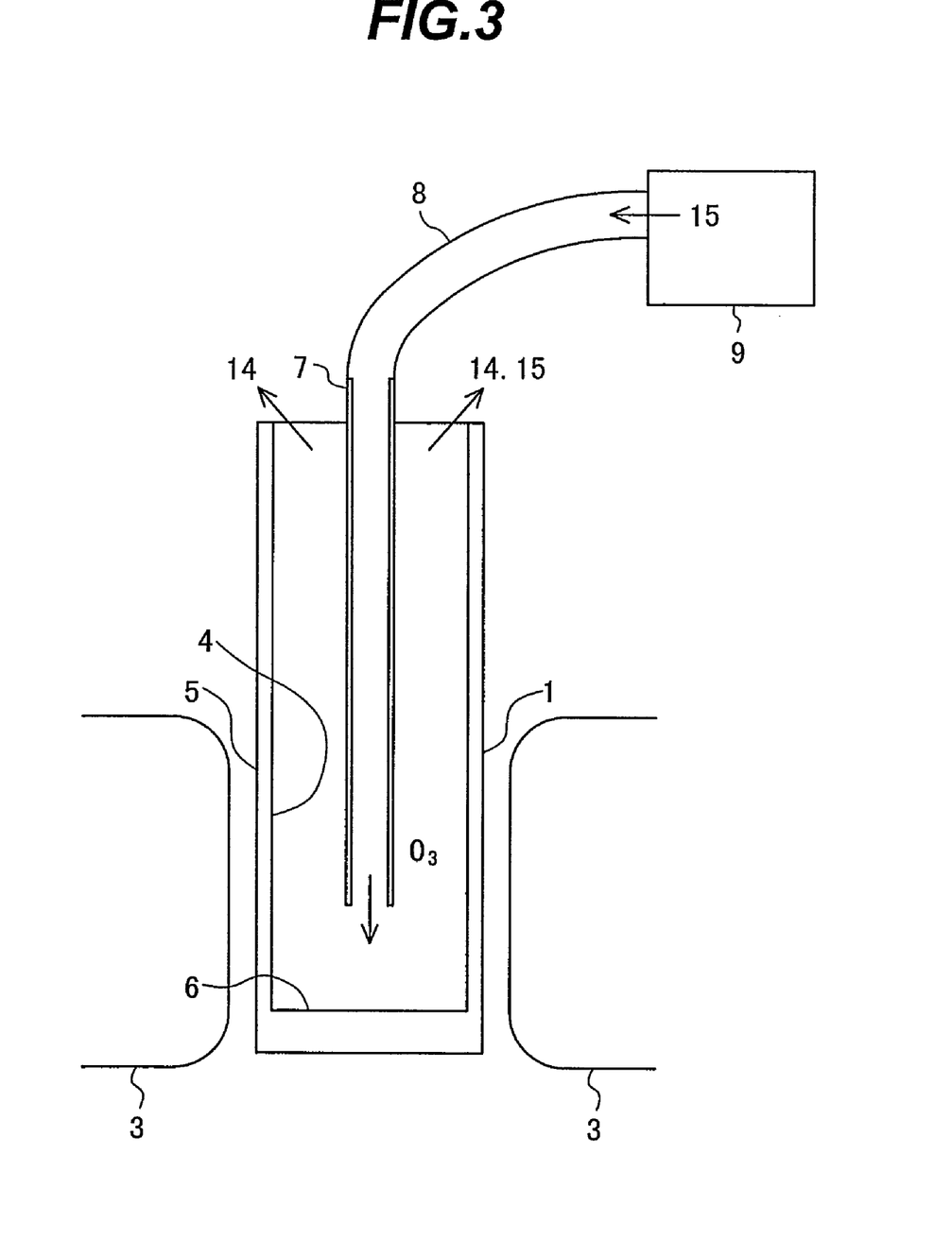
FIG. 3 is a block diagram illustrating a configuration in which a process gas is introduced using the hollow electrode (the first embodiment) in a third example of the present invention.

FIG. 3 is a view illustrating a configuration in which a process gas is used.

The reaction cuvette 1 is placed between the electrodes 3 facing each other, and the hollow electrode 7 is inserted into the reaction cuvette 1. The hollow electrode 7 is connected to a high voltage side of a high-voltage power supply, and the electrodes 3 are grounded.

The gas mixer 10 and the hollow electrode 7 are connected to each other via the piping 8. While a process gas 15 containing a rare gas is introduced into the reaction cuvette 1, a high voltage is applied to a section between the hollow electrode 7 and the opposed second electrode 3 to generate electric discharge between the electrodes.

Once the rare gas fed from the gas mixer 10 is excited due to electron collision, it shifts to the metastable state.

Thus, because the gas in the reaction cuvette is at a high energy level, electric discharge can easily be generated in the stable state.

Highly reactive radicals such as active oxygen species generated by the electric discharge is used to made hydrophilic the inner wall surface 4, the bottom 6, and the outer wall surface 5 of the reaction cuvette 1.

Because ozone which is one type of active oxygen species has a long life, it is necessary to introduce a process gas and also to discharge the air containing ozone to outside of the reaction cuvette 1. After the completion of electric discharge, clear air or an inactive gas such as nitrogen gas is introduced to prevent the product from being denatured.

With the operation, it is possible to overcome the problem in the conventional technology that surface portions are made unnecessarily hydrophilic by ozone residing after the completion of electric discharge so that only necessary surface portions are made hydrophilic.

EXAMPLE 4

Figure 4:
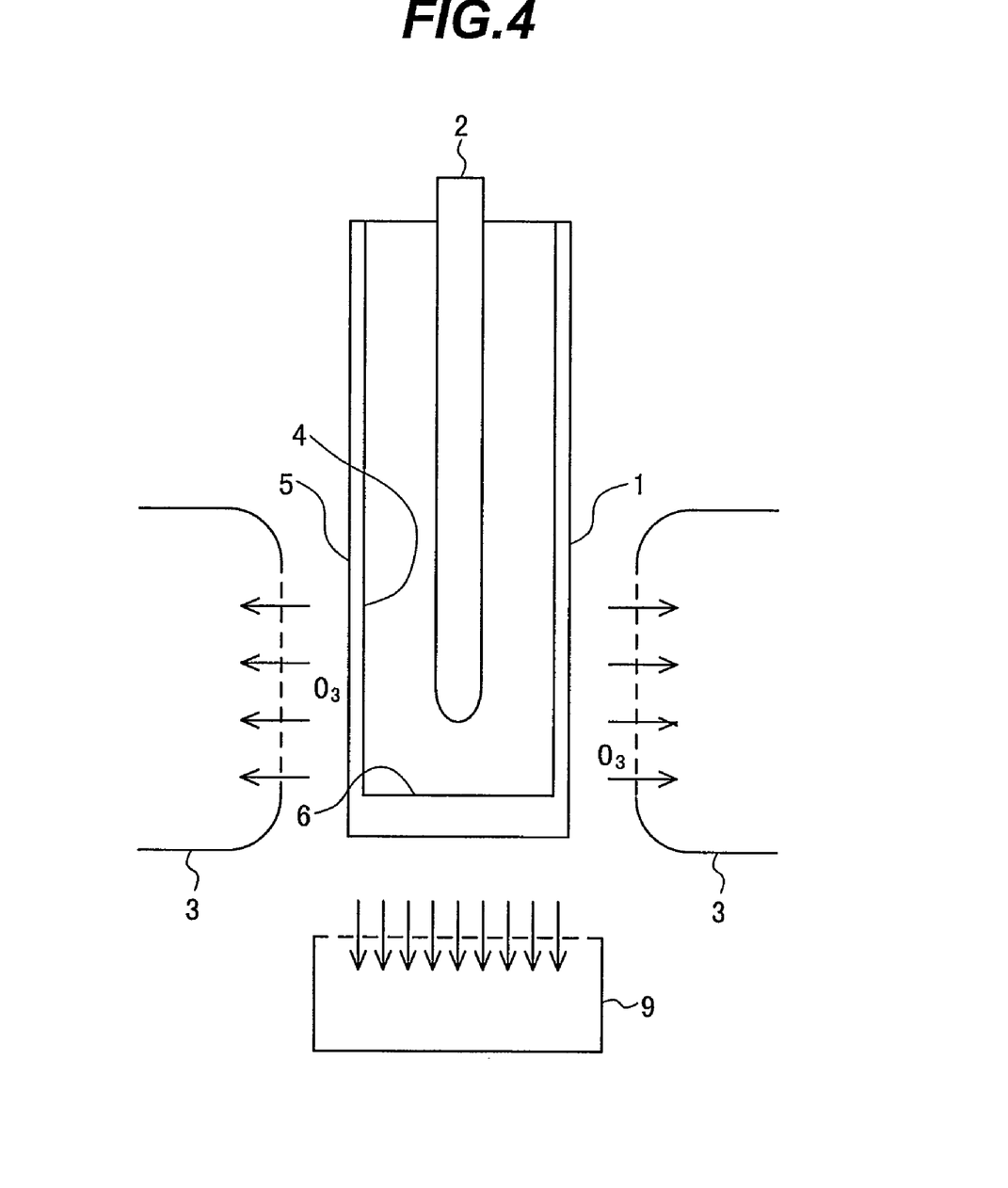
FIG. 4 is a block diagram illustrating a configuration in which a gas around a second electrode is discharged in a fourth example of the present embodiment.

FIG. 4 is a view illustrating a configuration in which a gas outside a reaction cuvette is sucked.

The reaction cuvette 1 is placed between the electrodes 3 facing each other, and the electrode 2 is inserted into the reaction cuvette 1.

The electrode 2 is connected to the high voltage side, and the electrodes 3 are grounded.

Gases such as ozone generated during electric discharge are discharged through a gas decomposer 9 such as activated carbon from a gas exhaust port provided under the opposed second electrodes 3.

Thus, because the processing can be performed in the same atmosphere as that prior to start of the processing, portions of an outer surface of the reaction cuvette can be prevented from being made unnecessarily hydrophilic.

EXAMPLE 5

Figure 5:
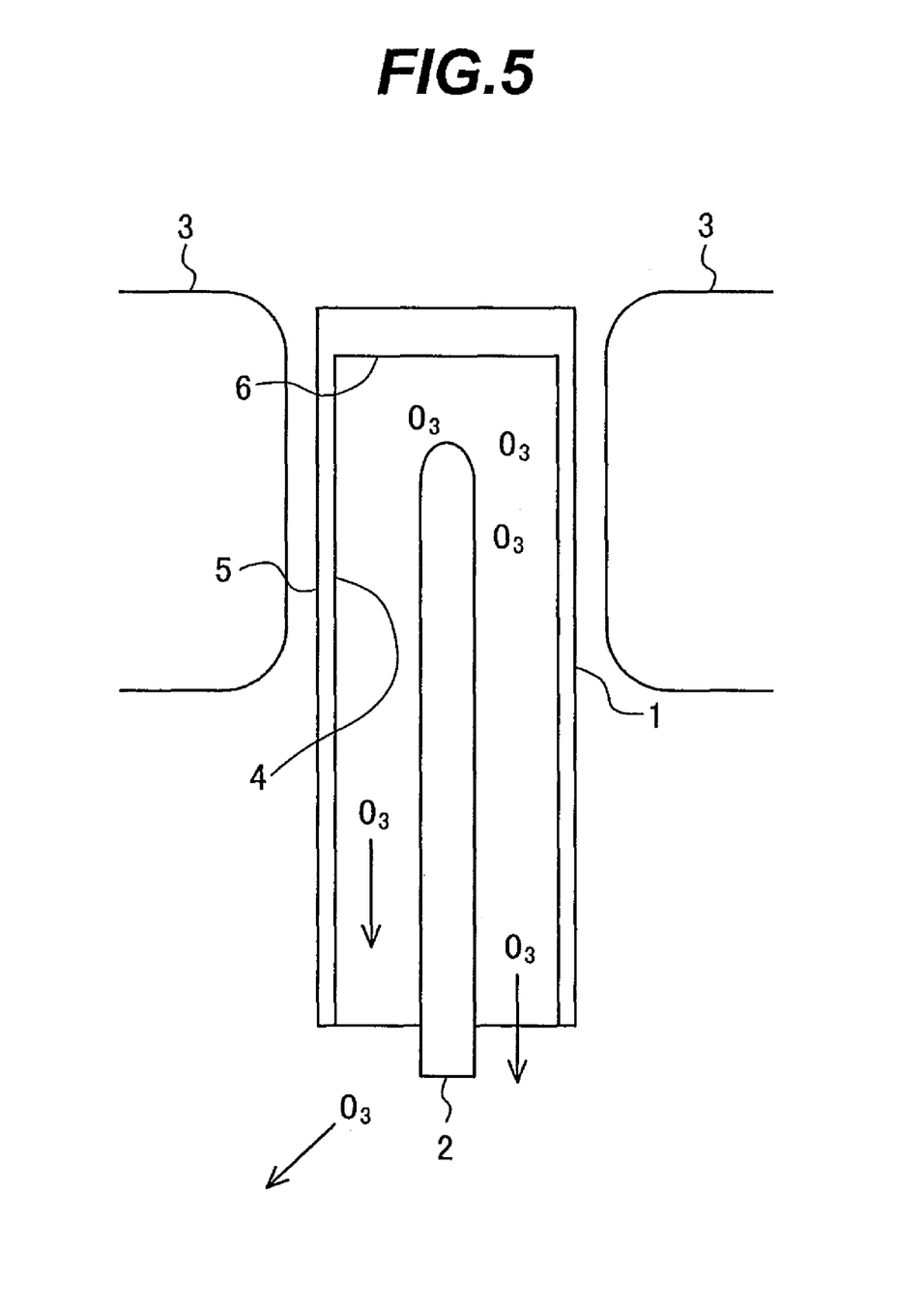
FIG. 5 is a block diagram illustrating a configuration in which an opening of a reaction cuvette faces downward in a fifth example of the present invention.

FIG. 5 is a view illustrating a configuration in which a reaction cuvette is placed upside down.

The reaction cuvette 1 is placed between the electrodes 3 facing each other with the opening facing downward, and the electrode 2 is inserted into the reaction cuvette 1 from the underside.

The electrode 2 is connected to a high voltage side of a high-voltage power supply, and the opposed second electrodes 3 are grounded. When the processing is performed with the arrangement described above, gasses heavier than air such as ozone can be naturally discharged. Therefore, the processing can be performed in the stable state without any positive ventilation facility.

Further, because it is possible to prevent dusts or other foreign materials from coming into the reaction cuvette 1 from the outside, a quality of the reaction cuvette is improved.

EXAMPLE 6

Figure 6A:
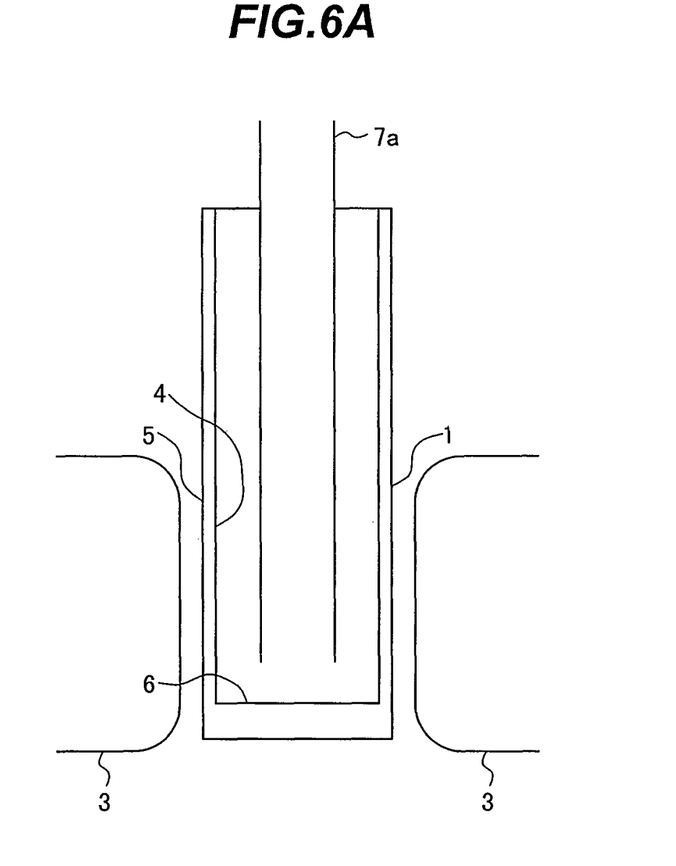
Figure 6B:
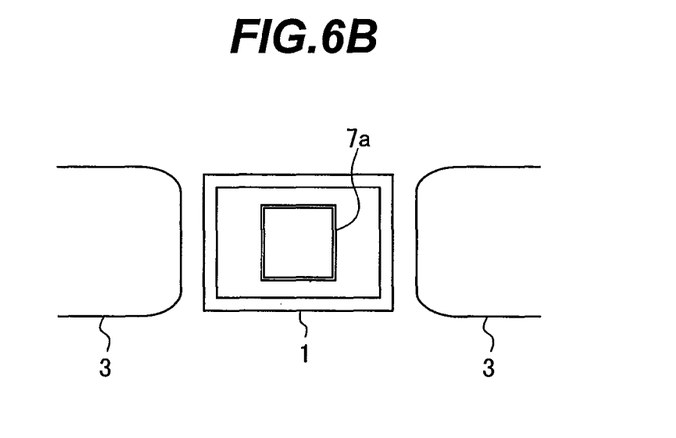
FIG. 6B is a plan view.

FIG. 6 is a view illustrating a configuration in which a hollow electrode having a rectangular cross section is used.

The reaction cuvette 1 is placed between the electrodes 3 facing each other, and a hollow electrode 7a having a rectangular cross section is inserted into the reaction cuvette 1. Then the hollow electrode 7a having a rectangular cross section is connected to a high voltage side of a high-voltage power supply, and the electrodes 3 are grounded.

As shown in 3, the hollow electrode 7a is connected to the gas decomposer 9 via the piping 8. A high voltage is applied to a section between the hollow electrode 7a and the opposed electrodes 3 to generate electric discharge between the electrodes.

Then, highly reactive radicals such as active oxygen species generated during electric discharge are used to made hydrophilic the inner wall 4, the bottom 6, and the outer wall 5 of the reaction cuvette 1.

Because the hollow electrode 7a has a rectangular cross section, an intensive electric field can be generated at corners of the reaction cuvette 1.

Thus, four corners of the reaction cuvette 1, to which otherwise air bubbles would easily adhere, can effectively be made hydrophilic.

In addition, air inside the reaction cuvette 1 is sucked through the hollow electrode 7a during electric discharge, and are discharged through the gas decomposer 9 such as activated carbon.

Thus, because an atmospheric gas not containing ozone always flows into the reaction cuvette 1, portions of an outer surface of the reaction cuvette can be prevented from being made unnecessarily hydrophilic.

EXAMPLE 7

Figure 7A:
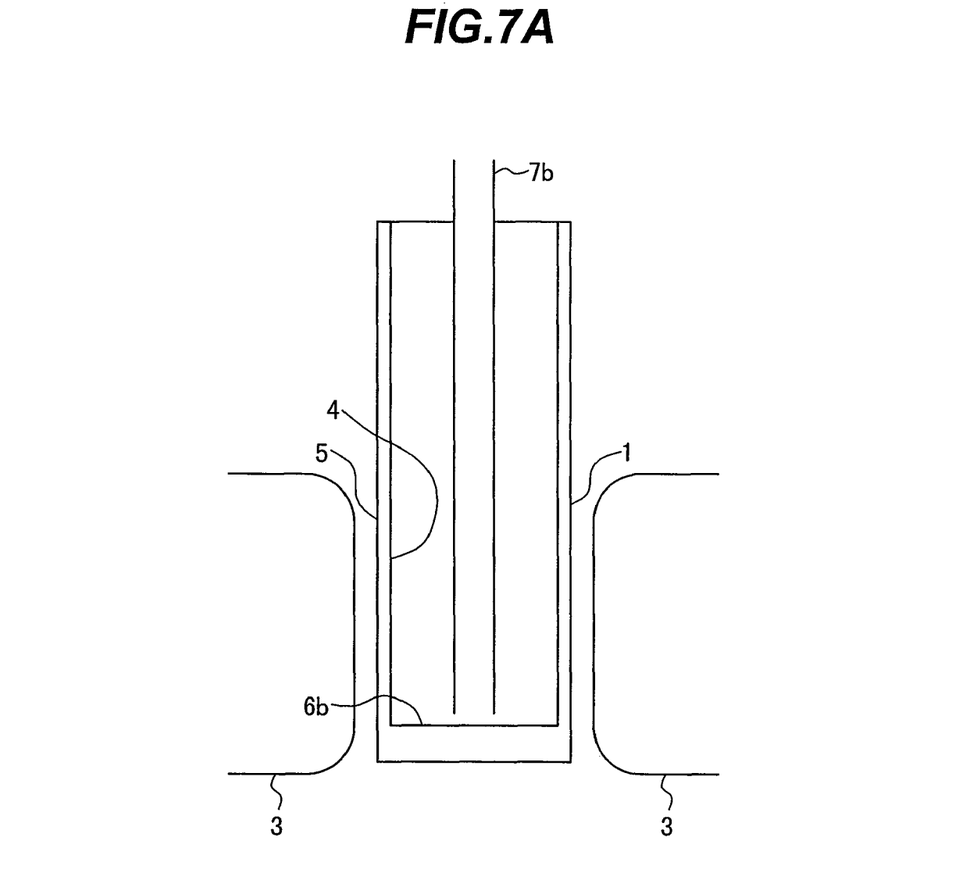
Figure 7B:
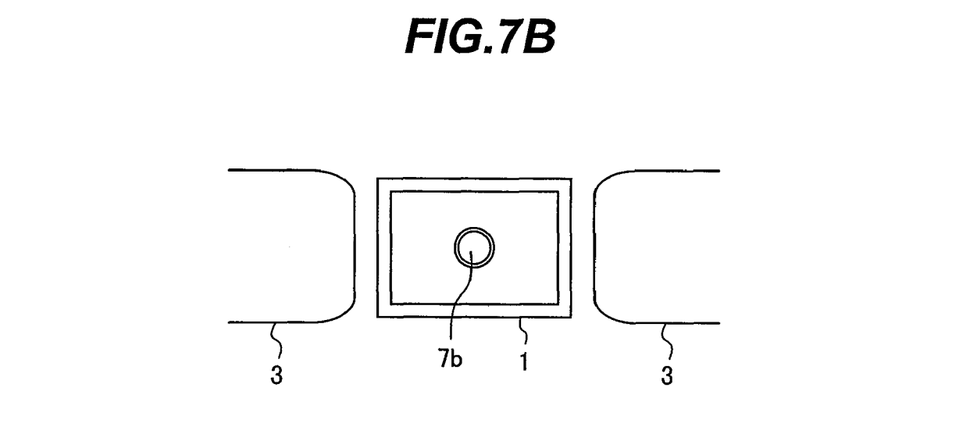
FIG. 7B is a plan view.

FIG. 7 is a view illustrating a configuration in which the processing for making a surface of a reaction cuvette hydrophilic is performed locally using a hollow electrode.

The hollow electrode 7 is connected to a high voltage side of a high-voltage power supply, and the electrodes 3 facing each other are grounded. The reaction cuvette 1 is placed between the opposed second electrodes 3, and the hollow electrode 7 is inserted into the reaction cuvette 1 up to a position close to the bottom 6 of the reaction cuvette 1.

A high voltage is applied to a section between the hollowing electrode 7 and the electrode 3 to generate electric discharge between the electrodes.

In this process, a non-electrified area 7b within the hollow electrode 7 is closed to a bottom of the reaction cuvette, and therefore only a bottom 6b of the reaction cuvette 1 just below the hollow electrode 7 can be prevented from being made hydrophilic.

Then, highly reactive radicals such as active oxygen species generated during electric discharge are used to made hydrophilic the inner wall 4, the bottom 6b, and the outer wall 5 of the reaction cuvette 1.

Figure 8:
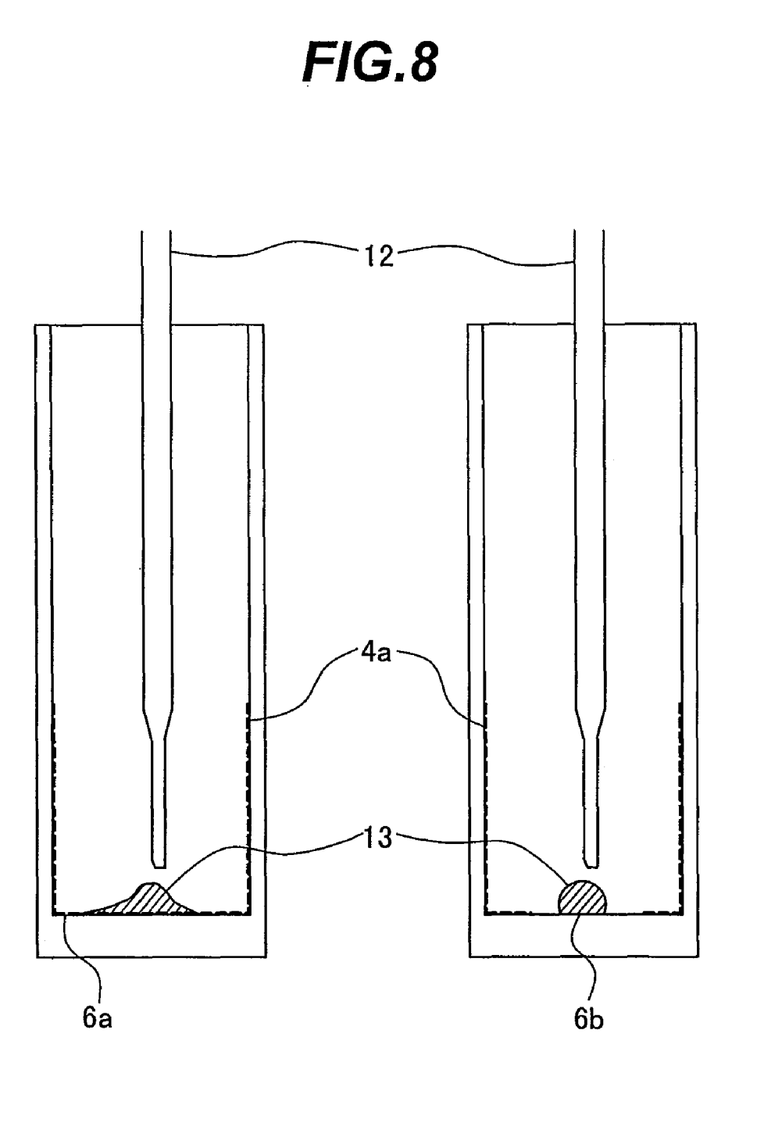
FIG. 8 is a seventh example of the present invention, and is a conceptual view showing a comparison between a case where a portion of a bottom portion of a reaction cuvette is made hydrophilic and a case where the portion of the bottom portion of the reaction cuvette is not made hydrophilic, with a sample probe inserted.

FIG. 8 is a view illustrating a case where a dispensing operation is performed to a bottom of the reaction cuvette 1 by using a sample probe 11.

When a sample 12 is dispensed onto a hydrophilic surface 6a of a bottom of the reaction cuvette 1 whose entire surface is made hydrophilic, wettability is high in the hydrophilic surface 6a and thereby the dispensed sample 12 spreads on the bottom surface of the reaction cuvette 1, namely the sample liquid is dispensed by an amount larger than a pre-specified value.

To overcome the problem, a sample liquid is dispensed onto a hydrophobic area 6b of a bottom surface of the reaction cuvette like in the conventional technology, so that the sample liquid can accurately be injected without requiring any specific change. Because portions other than the bottom surface are hydrophilic, such troubles as adhesion of air bubbles can be prevented.

EXAMPLE 8

Figure 9:
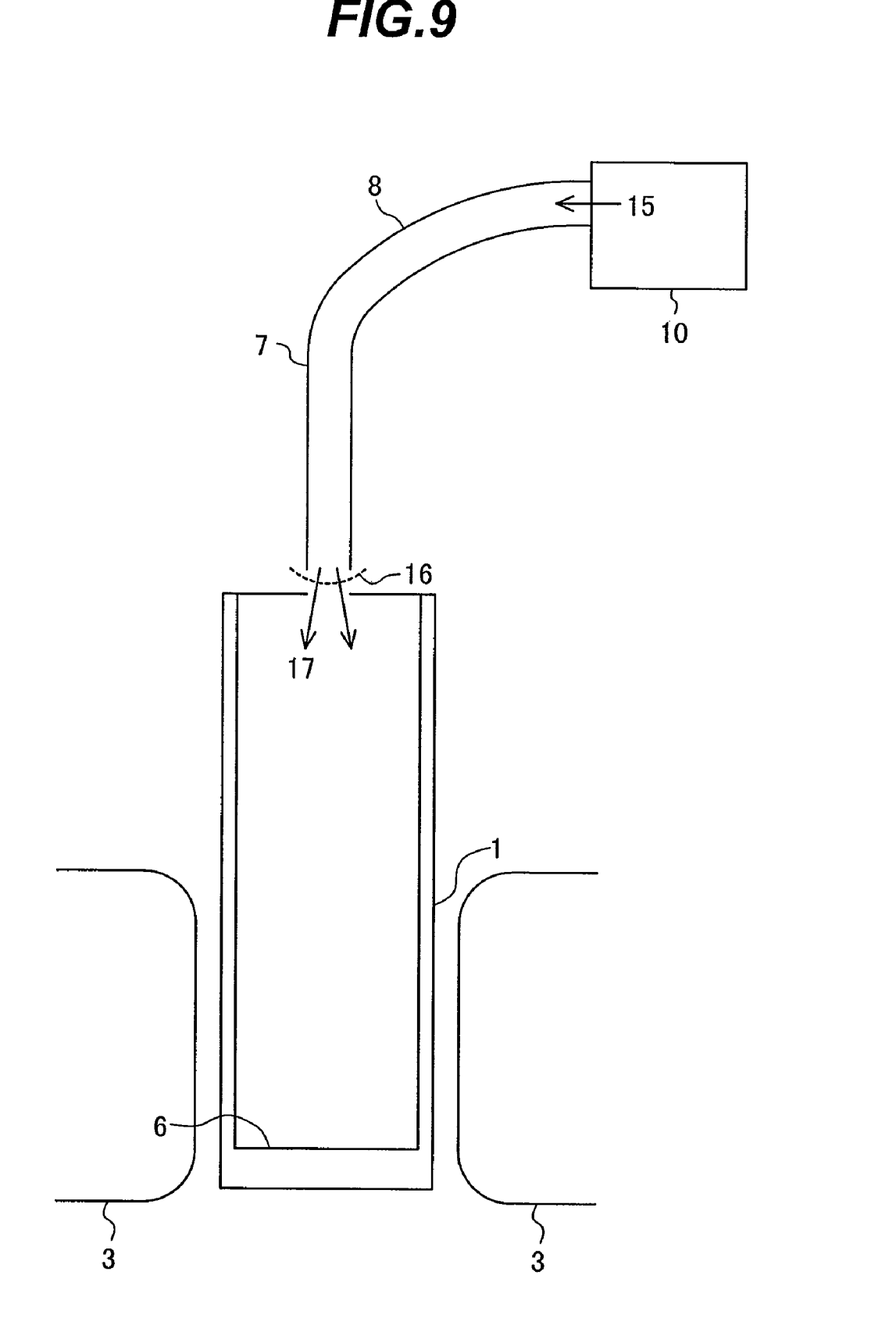
FIG. 9 is a block diagram illustrating a configuration in which a hollow electrode is used as a nozzle for a neutralization apparatus in an eighth example of the present invention.

FIG. 9 is a view illustrating a configuration in which removal of electricity is performed with the hollow electrode 7.

Air is made to flow in the first hollow electrode 7 having a rectangular opening at a position higher than a position at which an opening of the reaction cuvette 1 is located (referred to as a hollow electrode hereinafter).

Then, a high voltage is applied to the hollow electrode 7. Because a distance between the hollow electrode 7 and the electrode 3s facing each other is large, corona discharge is generated at a position close to a free end of the hollow electrode 7.

Positively or negatively ionized air 17 is introduced through a corona discharge area 16 into the reaction cuvette 1 for removal of electricity. Then the hollow electrode 7 is inserted into the reaction cuvette 1 to generate electric discharge.

Thus, reduction of intensity of an electric field due to electrification of a reaction cuvette can be prevented, and it is possible to generate electric discharge between the electrodes in the stable state, which makes it possible to make necessary areas hydrophilic to a desired degree. Symbol 4a denotes a hydrophilic area in the reaction cuvette 1.

Other examples of the present invention are described below.

In the first electrode, a portion discharging electricity for making a surface area of a reaction cuvette hydrophilic is thicker than a portion not discharging electricity, and the portion discharging electricity is closer to the second electrode than the portion not discharging electricity. With this configuration, it is possible to prevent portions of a surface area of the reaction cuvette from being made unnecessarily hydrophilic.

Also the configuration is allowable in which an area made hydrophilic is present from a bottom of a reaction cuvette up to a midway to an opening, although this feature is common to other examples.

This is based on the fact that a height of the second electrode is lower than that of the reaction cuvette in the depth direction. With this configuration, a range defined by the height of the second electrode is made hydrophilic by electric discharge. A border between an area made hydrophilic and an area not made hydrophilic extends in the lateral direction. Because of the feature, the border between an area made hydrophilic and an area not made hydrophilic is very clear.

In the examples described, electric discharge is performed in the form of corona discharge in most cases. This type of electric discharge can generate ozone used for making a surface of a reaction cuvette hydrophilic in the stable state.

Furthermore, descriptions are provided for an example in which only inner wall surfaces of a reaction cuvette are made hydrophilic below.

The first electrode 2 is inserted into the reaction cuvette 1 having a plate made from the same material as that of the reaction cuvette 1 overlaid on the outer wall surface thereof, and the corresponding second electrode is placed outside the reaction cuvette 1. The first electrode 2 is a high voltage side of a high-voltage power supply, and the second electrodes 3 facing each other are grounded.

A voltage is applied to a section between the first electrode 2 and the second electrodes 3 to generate electric discharge. Highly reactive radicals such as active oxygen species generated during electric discharge are used to make hydrophilic only an inner wall surface 4 of the reaction cuvette.

What is claimed is:

1. A method of manufacturing a reaction cuvette for an automatic analyzer in which a sample and a reagent are mixed with each other and its concentration is measured, the method comprising the steps of:
   providing a first electrode, which is inserted inside the reaction cuvette and having a hollow shape;
   providing second electrodes outside the reaction cuvette in such a manner that the second electrodes face each other; and
   making at least an inner surface of the reaction cuvette hydrophilic by electric discharging based on discharge generated by voltages applied to the first and second electrodes;
   wherein a gas containing ozone generated in the electric discharging is discharged with the first electrode.

2. The method of claim 1,
   wherein the first electrode has an air inlet hole provided at a free end of the electrode and/or around the electrode, and the gas is discharged therethrough.

3. The method of claim 1, wherein the automatic analyzer comprises a gas decomposing device which decomposes the ozone contained in an exhaust gas discharged from the inside of the reaction cuvette.

4. The method of claim 1,
   wherein the first electrode has an injection port provided at a free end of the first electrode and/or around the first electrode, and
   the automatic analyzer comprises a gas mixer which supplies a process gas used for processing the gas containing ozone generated in the electric discharging into the reaction cuvette via the first electrode.

5. The method of claim 4,
   wherein the process gas contains a dilution gas.

6. The method of claim 4,
   wherein the process gas is heated.

7. The method of claim 1, further comprising the step of:
   discharging or diluting the gas containing ozone generated around the reaction cuvette in the electric discharging.

8. The method of claim 7,
   wherein the automatic analyzer comprises a gas decomposing device for sucking and processing the gas containing ozone generated, the gas decomposing device being provided at a position under the bottom of the reaction cuvette.

9. The method of claim 7,
   wherein the gas containing generated ozone is sucked from the second electrodes and discharged.

10. The method of claim 1,
    wherein the reaction cuvette has a container-like form with its upper portion opened to provide an opening and its lower portion closed to form a bottom, and
    hydrophilic treatment is performed with the reaction cuvette turned upside down.

11. The method of claim 1,
    wherein the first electrode has a rectangular form in cross-section in the lateral direction, and
    the second electrode has a flat end face opposed the first electrode via the reaction cuvette and is placed in parallel to the first electrode.

12. The method of claim 1,
    wherein the first electrode is formed such that a portion discharging electricity is thicker than a portion not discharging electricity, and the portion discharging electricity is closer to the second electrode than the portion not discharging electricity.

13. The method of claim 1,
    wherein the reaction cuvette has a container-like form with its upper portion opened to provide an opening and its lower portion closed to form a bottom,
    the area subjected to hydrophilic treatment is present from a bottom portion of the reaction cuvette up to a midway to the opening, and
    a height of the second electrode in the depth direction of the reaction cuvette is substantially the same as that of the area subjected to hydrophilic treatment.

14. The method of claim 1,
    wherein the first electrode has a free end that is open, and
    the free end of the first electrode is provided at a position away by 1 mm or below from the bottom surface of the reaction cuvette for hydrophilic treatment.

15. The method of claim 1, further comprising the step of removing electricity within the reaction cuvette before a surface of the reaction cuvette is made hydrophilic.

16. A method of performing a surface treatment of a reaction cuvette for an automatic analyzer in which a sample and a reagent are mixed with each other and its concentration is measured, the method comprising the steps of:
    preparing a first electrode which is to be inserted inside the reaction cuvette;
    preparing second electrodes which is to be provided outside the reaction cuvette in such a manner that the second electrodes face each other;
    inserting the first electrode inside the reaction cuvette and providing the second electrodes outside the reaction cuvette;
    applying voltages to the first electrode and the second electrodes to subject at least an inner surface of the reaction cuvette to hydrophilic treatment by electric discharging; and
    discharging a gas containing ozone generated in the electric discharging from the reaction cuvette and then introducing air into the reaction cuvette.

* * * * *